(12) United States Patent
Umiastowski

(10) Patent No.: US 6,452,992 B1
(45) Date of Patent: Sep. 17, 2002

(54) METHOD AND DEVICE FOR MEASURING THE RELATIVE PROPORTIONS OF PLUTONIUM AND URANIUM IN A BODY

(75) Inventor: Krzysztof Umiastowski, Meudon (FR)

(73) Assignee: Commissariat A. l'Energie Atomique, Paris (FR)

(*) Notice: Subject to any disclaimer, the term of this patent is extended or adjusted under 35 U.S.C. 154(b) by 0 days.

(21) Appl. No.: 09/424,425

(22) PCT Filed: Jun. 5, 1998

(86) PCT No.: PCT/FR98/01151

§ 371 (c)(1),
(2), (4) Date: Dec. 27, 1999

(87) PCT Pub. No.: WO98/55883

PCT Pub. Date: Dec. 10, 1998

(30) Foreign Application Priority Data

Jun. 7, 1997 (FR) .............................. 97 07049

(51) Int. Cl.⁷ .......................... G01T 1/167; G21G 1/06
(52) U.S. Cl. ..................... 376/170; 376/153; 376/154; 376/157
(58) Field of Search ................. 376/153, 154, 376/157, 170

(56) References Cited

U.S. PATENT DOCUMENTS

| | | | | |
|---|---|---|---|---|
| 2,902,613 A | * | 9/1959 | Baldwin et al. ............. 313/61 |
| 3,293,434 A | * | 12/1966 | Dexter et al. ............... 376/157 |
| 3,496,357 A | * | 2/1970 | Weinzierl et al. .......... 250/83.1 |
| 3,636,353 A | * | 1/1972 | Untermyer ................. 250/83.1 |
| 4,320,298 A | * | 3/1982 | Buford, Jr. et al. ..... 250/358 R |
| 4,483,816 A | * | 11/1984 | Caldwell et al. ............ 376/158 |
| 4,497,768 A | * | 2/1985 | Caldwell et al. ............ 376/153 |
| 4,617,169 A | * | 10/1986 | Brodzinski et al. ......... 376/257 |
| 4,620,100 A |   | 10/1986 | Schoenig, Jr. et al. |
| 5,002,721 A | * | 3/1991 | Bernard et al. ............. 376/159 |
| 5,160,696 A | * | 11/1992 | Bowman ..................... 376/189 |
| 5,495,106 A | * | 2/1996 | Mastny ....................... 250/253 |

FOREIGN PATENT DOCUMENTS

| FR | 2 547 061 | 12/1984 | |
|---|---|---|---|
| WO | 13900 | * 11/1990 | ................. 376/153 |
| WO | 11388 | * 3/1997 | ................. 376/153 |

* cited by examiner

Primary Examiner—Michael J. Carone
Assistant Examiner—Jack Keith
(74) Attorney, Agent, or Firm—Pearne & Gordon LLP

(57) ABSTRACT

The invention relates a device for measuring the relative proportions of uranium and plutonium in a radioactive package (16), having:
- a source of photons (10) for irradiating the package,
- at least one delayed neutron detector (18) able to deliver counting signals for neutrons emitted by the package,
- means (22, 30) of acquiring counting signals, able to establish a decrease over time in the neutrons emitted, characteristic of the radioactive package,
- calculation means (32) for comparing the decay characteristic of the radioactive package with the respective characteristic decays of uranium and plutonium and for establishing relative proportions of uranium and plutonium in the package.

6 Claims, 3 Drawing Sheets

METHOD AND DEVICE FOR MEASURING THE RELATIVE PROPORTIONS OF PLUTONIUM AND URANIUM IN A BODY

DESCRIPTION

1. Technical field

The present invention relates a method and device for measuring the relative proportions of plutonium and uranium in a body.

It applies notably to the differentiation of plutonium and uranium contained in large packages of radioactive waste. Large package means concreted waste barrels with a diameter of around one meter or more, or metallic containers whose volumes can be as much as several cubic meters.

It is in fact important, during the storage of radioactive waste, to know the nature and activity of the radioemitters and in particular of the actinides, that is to say essentially uranium and plutonium.

2. Prior Art

The known methods of determining the actinide content of a body can be classified into two categories. In fact the so-called "destructive" methods are distinguished from the so-called "non-destructive" methods.

When destructive methods are used, samples are taken by cutting the package of radioactive material. The samples taken are then analysed using different analysis techniques, amongst which chemical analysis, X-ray fluorescence, gamma spectrometry or neutron activation can be mentioned, for example.

The methods mentioned above are applicable only to samples with a small volume, from a few cubic centimeters to a few liters. They are therefore ineffective for non-destructive measurements of radioactive waste packages of large size.

Amongst the methods of determining the actinide content known as non-destructive, there are also two sub-categories comprising respectively the active non-destructive methods and the passive non-destructive methods.

The passive non-destructive methods are essentially methods of spectrometry of the gamma radiation emitted by the body, counting the neutrons emitted during the spontaneous fission of the actinides contained in the body, or calorimetry.

The method of gamma spectrometry of the radiation emitted is also applicable only to homogeneous samples of small size. This is because counting the neutrons emitted during the spontaneous fission of the actinides in larger samples requires sophisticated equipment, notably for being free of the influence of neutrons coming from sources other than the spontaneous fission of the body to be measured.

The calorimetry method makes it possible to evaluate the total quantity of heat released in a radioactive body, such as a package of waste. It does not however make it possible to determine the type of disintegration which gives rise to the heat.

Finally, active non-destructive methods are known for determining the actinide content of a body. These methods are said to be active because they use a radiation source known as interrogating radiation, external to the radioactive body.

Amongst these active non-destructive methods, there are the measurements of attenuation and the measurements of emitted radiation.

Measurements of attenuation, such as gamma measurement or tomography, measure the attenuation of an external radiation passing through the radio package to be examined. The measurements of emitted radiation, on the other hand, measure a radiation coming from the package itself and caused by an external interrogation radiation. The latter measurements are well adapted to an examination of packages of radioactive waste of large size such as concrete containers. However, the active non-destructive methods known at the present time make it possible only to determine the total quantity of actinides present in a package, without any distinction with regard to their nature or composition. In particular, they do not make it possible to differentiate the uranium from the plutonium contained in the body or radioactive package examined.

DISCLOSURE OF THE INVENTION

The aim of the present invention is an analysis method and device which does not have the limitations mentioned above.

Another obvious aim is to propose a non-destructive measuring method and device which make it possible to differentiate uranium and plutonium in radioactive waste packages.

In order to achieve these aims, the object of the invention is more precisely a method of measuring relative proportions of uranium and plutonium in a body, including the following steps:

a) irradiating the body with photons whose energy is sufficient to cause photofission of actinide elements, b) counting the number of delayed neutrons emitted per unit time by fission products induced in the said body in response to the irradiation, c) establishing a time decay function of the number of neutrons $n_e(t)$ emitted, characteristic of the actinide composition of the said body, d) comparing the time decay $n_e(t)$ characteristic of the actinide composition of the said body, with time decays of emission of delayed neutrons $n_u(t)$, $n_p(t)$ characteristic respectively of uranium and plutonium, in order to establish the relative proportions of these elements in the body.

Thus the invention is essentially based on the photon activation of the actinides and on the measurement of decrease over time in the number of delayed neutrons.

Unlike neutron activation, which suffers from the short travel of the neutrons in materials containing hydrogen, such as concrete or bitumen, photon activation, used in the method of the invention, proves particularly adapted to waste packages of large size. The attenuation of the photons, notably of the photons with an energy greater than 10 MeV, is in fact low.

Moreover, the detection and counting of delayed fission neutrons has, compared with the counting of prompt neutrons, the advantage of freeing the measurement from the reactions on the nuclei of the matrix containing the radioactive waste. These reactions are in fact added to the phenomenon of photofission of the actinide nuclei during the photon activation.

The prompt neutrons are emitted during fission, and therefore during the gamma irradiation pulse period. The gamma photons also give rise to neutrons, through the neutron-gamma (n, γ) reaction induced in the different elements. It is not possible to make a distinction between the prompt fission neutrons and the neutrons originating from the neutron-gamma (n, γ) reactions.

The photonuclear reaction of the photons on the actinide nuclei takes place in two steps contained within an interval of time of around one picosecond. A photon is first of all absorbed by the nucleus. The absorbed energy then causes the emission of a photon or one or more particles. When the absorbed energy is greater than the fission threshold of the nucleus it causes on the other hand the fission of the latter.

The effective cross section of absorption of a photon by the atomic nucleus varies with the energy of the photon. For a photon whose energy is less than approximately 6 MeV, very narrow absorption resonances are observed, with a width of approximately 1 eV. On the other hand, for photons with energies greater than 10 MeV, a very broad absorption resonance of several MeV is observed. The absorption resonance energy for photons is respectively 12.26 MeV and 12.24 MeV for uranium 238 and plutonium 239.

The energy of the photons used for irradiating the radioactive body is chosen so as to be sufficient to cause photofission of the actinide elements. In particular, it is chosen so as to be greater than the is photofission threshold, which is situated at approximately 6 MeV. It is preferably chosen so as to be greater than 10 MeV and close to the absorption resonance energy.

The radioactive body is preferably irradiated for a sufficiently long irradiation time to accumulate a sufficient number of fission products and consequently to obtain a significant emission of delayed neutrons. However, it is not necessary to prolong the irradiation unnecessarily. Thus the irradiation time is preferably chosen so as to be around the mean period of the delayed neutrons, that is to say around 10 to 20 seconds, for example.

After the irradiation of the radioactive body to be examined, a counting of the neutrons is effected, preferably in a multiscale mode. The multiscale mode consists of counting the number of neutrons detected in successive intervals of time with a unit width dt. The number of neutrons counted in each interval of time is recorded. The total measuring time $\Delta T_m$ is such that $\Delta T_m = Ndt$ where N is the number of time intervals.

The irradiation and counting steps can if necessary be repeated several times.

A following step of the method consists of establishing, according to the counting, a time decay in the neutrons emitted, characteristic of the fissile material. The time decay can be represented in the form of a curve.

This step can include calculations for correction of the relative abundance of the groups of delayed neutrons according to the experimental conditions and notably the irradiation conditions. The corrections are described below briefly.

It should be stated that, for all the fissile elements, the delayed neutrons are classified into six groups according to their decay periods. The values of these six periods are practically constant for all the fissile elements. On the other hand, the relative abundance of each group varies from one isotope to another. Table 1 gives the relative abundances and periods for uranium 238 and plutonium 239.

TABLE 1

| GROUP | U 238 | | Pu 239 | |
|---|---|---|---|---|
| | $T_{1/2}$ (s) | ABUNDANCE | $T_{1/2}$ (s) | ABUNDANCE |
| 1 | 52.38 | 0.013 | 53.75 | 0.038 |
| 2 | 21.58 | 0.137 | 22.29 | 0.280 |
| 3 | 5.00 | 0.162 | 5.19 | 0.216 |
| 4 | 1.93 | 0.388 | 2.09 | 0.328 |
| 5 | 0.493 | 0.225 | 0.549 | 0.103 |
| 6 | 0.172 | 0.075 | 0.216 | 0.035 |

The change over time in the number of delayed neutrons emitted by (pure) uranium 238 and (pure) plutonium 239 can be calculated easily, from the data in table 1.

This number is calculated in accordance with the formula:

$$n(t) = \sum_{k=1}^{6} \beta_k e^{-\lambda_k t}$$

where $\beta_k$ is the relative abundance of the group k of neutrons and $\lambda_k$ is the decay constant for the group k.

The relative abundances of the different groups of delayed neutrons correspond to the values at radioactive equilibrium, that is to say quantities accumulated after a very long irradiation, of a duration at least equal to several times the longest period of the group, that is to say at least 5 to 10 minutes.

However, according to a particular aspect of the invention, it is possible to irradiate the radioactive body either continuously or by means of a train of photon pulses.

By way of example, the photons can be delivered in the form of a train of macropulses of duration dt, with a frequency of repetition $f_r$. After a number N of pulses, the radiation is stopped, and the delayed neutrons are counted. If the duration of irradiation is short, radioactive equilibrium is not achieved and the relative abundances are different from those of equilibrium. Hereinafter, an example of calculation of corrections is set out by way of example.

The total number of fissions $n_f$ induced in the irradiated sample, by a macropulse, is equal to:

$$n_f = \Phi \Sigma_f dt \quad (1)$$

where $\Phi$ is the photon flow, $\Sigma_f$ is the effective cross section of photofission, and dt the macropulse duration.

On this number, a fraction $v_d$ of delayed neutrons is emitted. The number $n_{k,o}$ of delayed neutrons in the group k (k=1 . . . 6) is equal to:

$$n_{k,o} = n_f v_d \beta_k \quad (2),$$

where $\beta_k$ is the relative abundance of the group k.

The number of precursors (parent radioactive elements of the delayed neutron emitter), created during a macropulse i, which remain at the end of a sequence of N pulses, is:

$$n_{k,i} = n_{k,o} e^{-\lambda_k (Ni) t_r} \quad (3)$$

$\lambda_k$ being the radioactive constant of the group k, and $t_r$ being the repetition period of the macropulses.

The total number of precursors in the group k, at the end of irradiation, is:

$$n_k = \sum_{i=1}^{N} n_{k,i} = n_{k,0} \sum_{i=1}^{N} e^{-\lambda_k (N-i) t_r} \quad (4)$$

Expression (2) standardised to 1 delayed neutron ($n_f v_d = 1$) gives:

$$n_{k,o} = \beta_k \quad (5)$$

The sum in expression (4) is reduced as follows:

$$S_k = \sum_i \exp[-\lambda_k (N-i) t_r] = e^{N\alpha_k} e^{\alpha_k} \sum_i \exp[\alpha_k (i-1)] \quad (6)$$

$\alpha_k = \lambda_k t_r$, where $S_k$ is the correction factor of the number of neutrons in the group k.

The sum in expression (6) is the sum of a geometric series. Calculation gives:

$$S_k = \frac{e^{\alpha_k} - e^{-(N-1)\alpha_k}}{e^{\alpha_k} - 1} \quad (7)$$

Introducing (5) and (7) into (6) gives:

$$\beta_{k,o} = n_k = \beta_k S_k \quad (8)$$

The values of $\beta_{k,o}$ must be standardised, so that their sum is equal to 1:

$$\sum_{k=1}^{6} \beta_{k,0} = 1 \quad (9)$$

For calculating the decay of the delayed neutrons, taking account of the irradiation conditions, it is necessary to replace the value $\beta_k$, in the formula $$n(t) = \sum_{k=1}^{6} \beta_{k,} e^{-\lambda_k t},$$

indicated previously, by the value $\beta_k S_k$.

An example of the corrected values for uranium 238 is given in Table 2. The experimental conditions used in the calculation of the corrections are as follows:

duration of a macropulse dt=2.5 μs, frequency of repetition $f_r$=100 Hz, irradiation by a series of N=1500 macropulses (irradiation time 15 sec).

TABLE 2

| GROUP | $T_{1/2}$ s | $\lambda$ $s^{-1}$ | $\beta$ | S | $\beta S$ |
|---|---|---|---|---|---|
| 1 | 52.38 | 0.0132 | 0.013 | $5.238 \times 10^3$ | 0.1279 |
| 2 | 21.58 | 0.0321 | 0.137 | $2.158 \times 10^3$ | 0.5553 |
| 3 | 5.00 | 0.1386 | 0.162 | $5.005 \times 10^3$ | 0.1523 |
| 4 | 1.93 | 0.33591 | 0.388 | $1.935 \times 10^2$ | 0.1410 |
| 5 | 0.493 | 1.4060 | 0.225 | $4.980 \times 10^3$ | 0.0210 |
| 6 | 0.172 | 4.0299 | 0.075 | $1.770 \times 10^3$ | 0.0025 |

When the time decay of the delayed fission neutrons from the fissile material is established, it is compared with the characteristic decay of the neutrons $n_u(t)$ and $n_p(t)$ of pure uranium and plutonium. The characteristic decay of the neutrons of pure uranium and plutonium can be determined experimentally, or calculated directly, for example with the data in Table 1.

According to a particular aspect of the invention, it is possible to determine coefficients a and b such that: $n_e(t) = an_u(t) + bn_p(t)$, the coefficients a and b indicating the relative proportions of uranium and plutonium in the radioactive body.

The coefficients a and b can be determined, for example, by a so-called least squares method set out briefly below.

The decrease in the number of delayed neutrons emitted by the uranium, corrected according to the experimental conditions, is given by the following formula, already explained:

$$n_u(t) = \sum_k \beta_u S_{u,k} e^{-\lambda_k t} \quad (1)$$

The number of neutrons emitted by the plutonium is given by the similar formula:

$$n_p(t) = \sum_k \beta_p S_{p,k} e^{-\lambda_k t}$$

In these formulae the indices u and p of the parameters refer respectively to uranium and plutonium The total number of neutrons emitted by the mixture is given by the formula:

$$n(t) = an_u + bn_p \quad (2)$$

During measurement, the width of the counting interval is $\Delta t$ and the number of intervals is equal to m. The total counting time is therefore equal to:

$$t_m = m\Delta t \quad (3)$$

The number of pulses accumulated in an interval i is:

$$ci = \sum_1 a_1 \sum_{k=1}^{6} \beta_{1,k} S_{1,k} \exp(-\lambda_k t_i)[1 - \exp(-\lambda_k \Delta t)] \quad (4)$$

The number of neutrons counted in an interval of time i, during the multiscale counting, is designated by $Ce_i$.

The values of a and b are sought, which fulfil the condition:

$$Ce_i = c_i \quad (5a),$$

where $c_i$ is defined by formula (4).

This equation, in matrix form, is written generally in the form:

$$MX = Y \quad (5b)$$

where M, X and Y are the matrices defined as followed:

$$M_{i,1} = \sum_{k=1}^{6} \beta u, \quad (6a)$$

$$M_{i,2} = \sum_{k=1}^{6} \beta p, \quad (6b)$$

$$X = \begin{pmatrix} a \\ b \end{pmatrix}, \quad (6c)$$

$$Y_i = Ce_i, \quad (6d)$$

The values of $M_{i,1}$, $M_{i,2}$ and $Y_i$ are standardised as follows:

$$\sum_{i=1}^{m} M_{i,1} = 1, \quad (7a)$$

$$\sum_{i=1}^{m} M_{i,2} = 1, \quad (7b)$$

$$\sum_{i=1}^{m} Y_i = 1, \quad (7c)$$

The solution of equation (5b) is:

$$X=(M^TM)^{-1}(M^TY) \quad (8),$$

From the parameters a and b determined by formula (8), the uranium content $\tau_u$ is calculated:

$$\tau_u = \frac{a}{a+b}, \quad (9a)$$

and that of plutonium $\tau_p$:

$$\tau_p = \frac{b}{a+b}, \quad (9b)$$

The invention also relates a device for measuring relative proportions of uranium and plutonium in a radioactive package.

The device has:
- a source of activation photons for irradiating a radioactive package,
- at least one neutron detector, placed in the vicinity of an area for receiving the package, able to deliver counting signals for neutrons emitted by the package,
- means of acquiring the counting signals, able to establish a decrease over time in the number of neutrons emitted, characteristic of the radioactive package,
- calculation means for comparing the characteristic decay of the radioactive package with the respective characteristic decays of pure uranium and plutonium and in order to establish relative proportions of uranium and plutonium in the package.

The acquisition means and the calculation means can be produced for example in the form of an electronic acquisition card, connected to a microcomputer, with an appropriate calculation program.

According to a particular embodiment of the device, the photon source can include an electron accelerator provided with a Bremsstrahlung target.

According to a preferred implementation, the device can have from 4 to 7 neutron detectors disposed around the area for receiving the radioactive waste package.

The arrangement of the detectors and other characteristics and advantages of the invention will emerge more clearly from the description which follows, with reference to the figures of the accompanying drawings. This description is given by way of purely illustrative and non-limitative example.

DESCRIPTION OF EMBODIMENTS OF THE INVENTION

Figure 1:
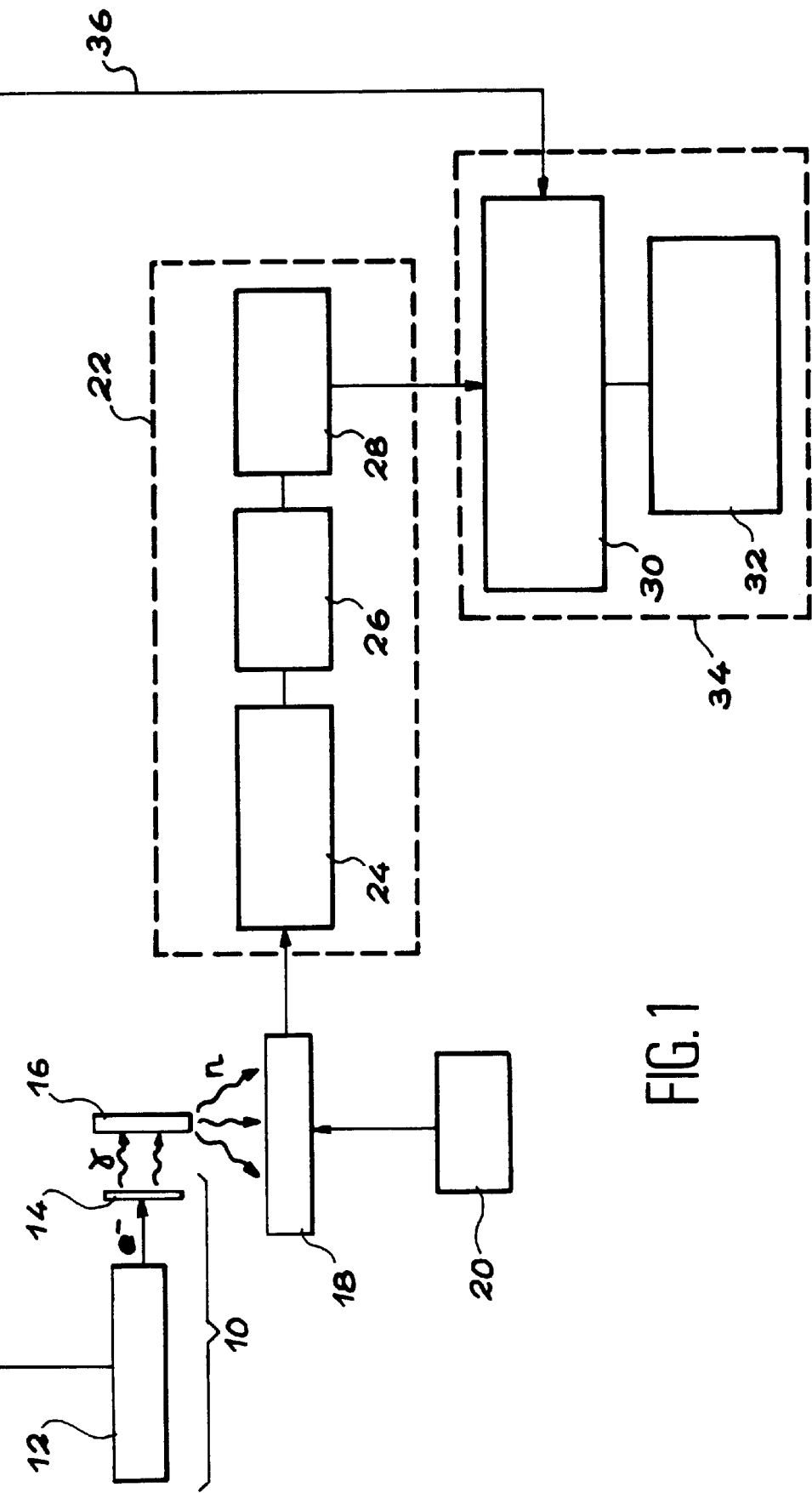
FIG. 1 is a simplified schematic representation of a device according to the invention.

FIG. 1 shows an experimental device according to the invention.

The device has a source of gamma activation photons indicated with the reference 10. The source of gamma photons has an electron accelerator 12 in front of which a so-called "Bremsstrahlung" target 14 is disposed. The target generally consists of a heavy metal. This is for example a sheet of tantalum with a thickness of 1.95 mm or a sheet of tungsten with a thickness of 1.7 mm.

The target converts the energy of the electrons of 15 to 16 MeV, for example, coming from the accelerator 12, into gamma photons.

The gamma photons, represented by arrows, are directed to a sample 16 or a package of radioactive material to be analysed. The sample contains actinides which, under the effect of the protons, undergo fission, and emit neutrons.

The reference 18 indicates a neutron detector unit placed close to the sample 16 in order to detect the delayed neutrons emitted by the sample.

The detector unit 18 has several detectors, filled with helium 3 and surrounded by a moderator made of polyethylene for example. All the detectors and the moderator are covered with a layer of cadmium or other thermal neutron absorbent. This layer serves essentially to decrease the background measuring noise due to neutrons generated, for example, in the neighbouring walls of the room in which the device is installed (not shown).

The detectors in the unit 18 are biased using a high-voltage source 20.

The detector unit 18 is connected with an acquisition chain 22 comprising essentially a current to voltage converter circuit 24, a shaping circuit 26 and a discriminator 28. Thus the pulses coming from the detector unit are amplified and shaped before being directed to an acquisition and counting card 30 connected to an analyser 32.

The counting card 30 and analyser 32 form part, for example, of a microcomputer 34.

An arrow 36 indicates a link between the electron accelerator 12 and the counting card 30 in order to transmit a starting signal indicating the start of the irradiation of the sample 18.

Figure 2:
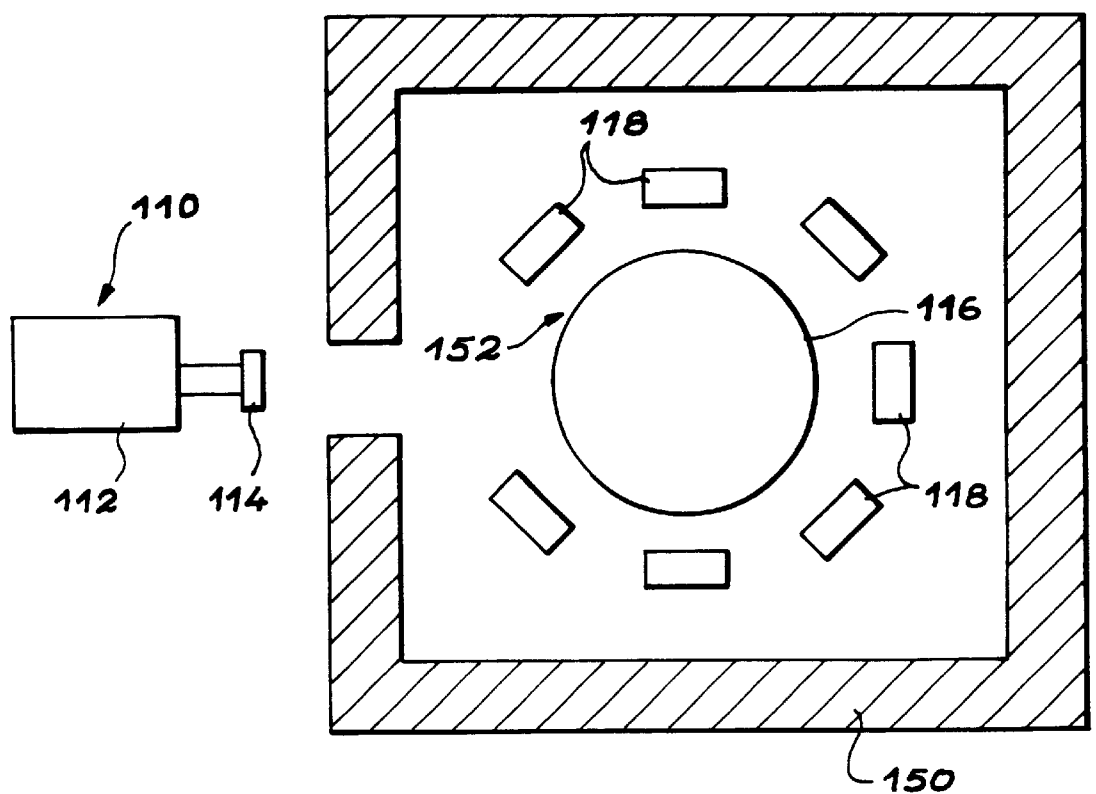
FIG. 2 is a horizontal section of a particular installation of the device of the invention.

FIG. 2 shows, in horizontal section, an installation for differentiating the uranium and plutonium in a package of radioactive waste.

The package of waste 116 is disposed in an enclosure 150. More precisely, the package is placed at the centre of a reception area 152 surrounded, for example, by seven neutron detector units 118 uniformly distributed around this area.

The enclosure 150 has an opening through which the package can be irradiated by a source of gamma photons 110. The source comprises an electron accelerator 112 and a Bremsstrahlung target 114 of the type already described with reference to FIG. 1.

The acquisition chain and the signal processing means, like the power supply sources of the detector units 118, are not depicted in FIG. 2 for reasons of simplification.

It can be noted that the function of the enclosure 150 is to protect the package and detectors from the influence of neutrons generated outside the reception area 152, for example in the walls of the installation room and any neighbouring objects.

The enclosure 150 incorporates a moderating material. According to a particular embodiment, all or some of the neutron detectors can be included within the walls of the enclosure 150.

Figure 3:
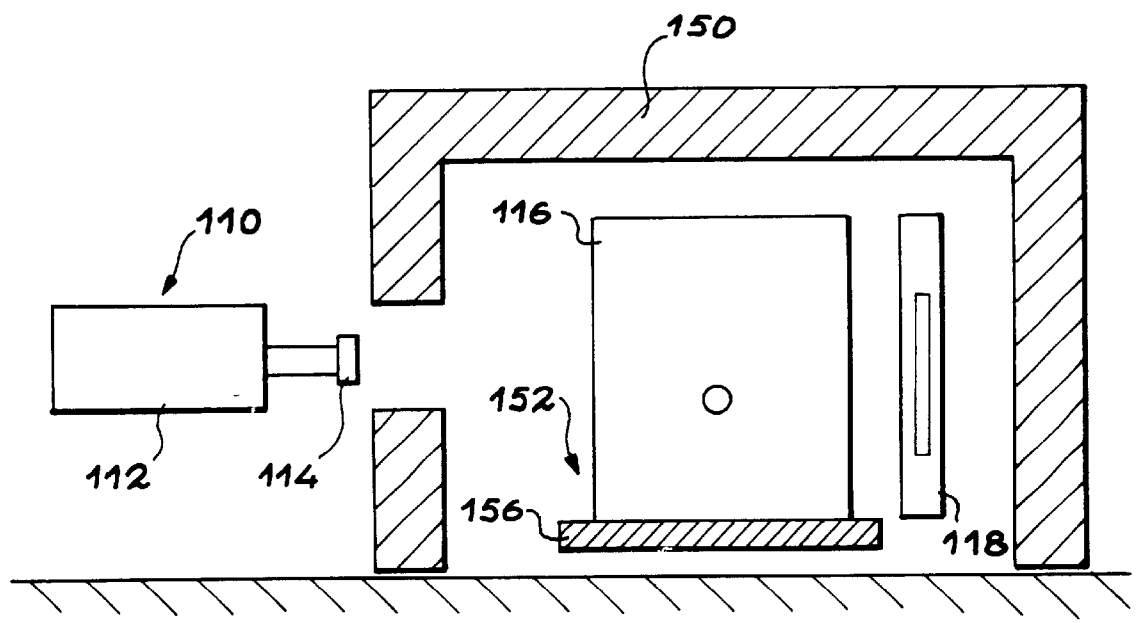
FIG. 3 is a transverse section of the installation in FIG. 2.

FIG. 3, which is a transverse section of the installation, shows that the package of waste 116 can be disposed on a rotary table 156, at the centre of the reception area 152.

The rotary table 156, set in rotation during the irradiation and during the measurement, makes it possible to obtain even irradiation and measurements of the radioactive waste package.

Figure 4:
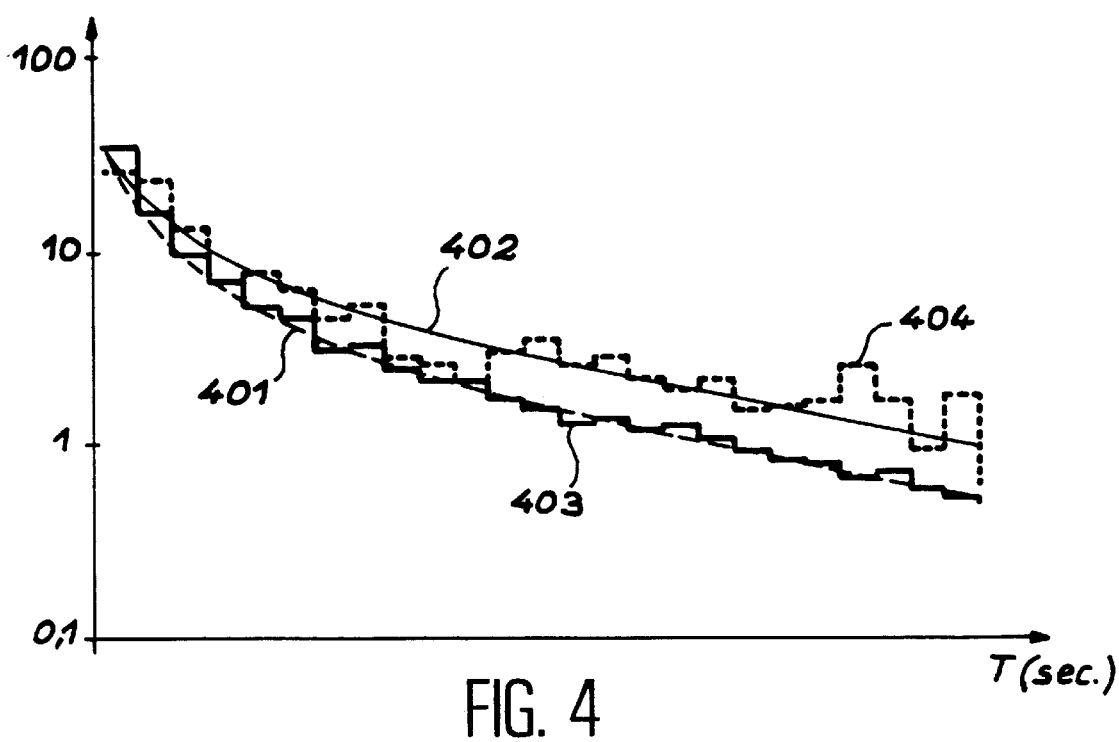
FIG. 4 depicts theoretical and experimental decay curves for pure uranium and plutonium.

FIG. 4 shows curves depicting the characteristic decays of pure uranium and plutonium. In FIG. 4, the number of neutrons counted is entered on the Y-axis on a logarithmic scale, whilst the time, measured in seconds, is indicated on the X-axis.

The curves 401 and 402 are theoretical decay curves, respectively of uranium and plutonium. The curves 403 and 404 are experimental decay curves respectively for uranium and plutonium, established in an experimental device as described previously.

In order to effect the measurements of the curves 403 and 404, the samples of uranium and plutonium are irradiated with a train of macropulses of gamma photons each with a duration of 2.5 $\mu$s and at a frequency of 100 Hz. The number of macropulses is 1,500, which corresponds to a total duration of irradiation of 15 seconds.

The countings of the neutrons for the curves in FIG. 4 are integrated over intervals of 6 seconds.

It should be stated that the parameters defined in the above two paragraphs relate a particular implementation and have no limitative character.

Figure 5:
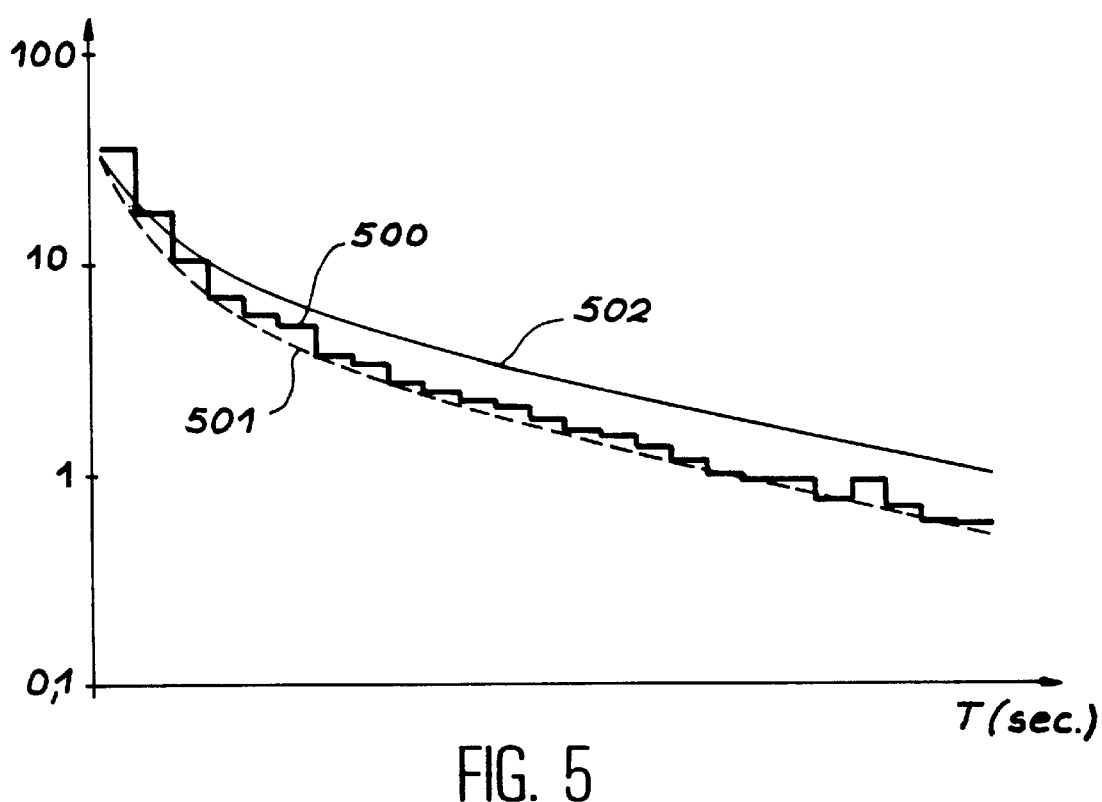
FIG. 5 depicts the theoretical decay curves for uranium and plutonium and an experimental decay curve for a sample containing both uranium and plutonium.

In FIG. 5, the curve 500 indicates the characteristic decay of a sample formed by a mixture of 87% uranium and 13% plutonium.

For information, the theoretical decay curves for uranium and plutonium are also entered. These curves are indicated with the references 501 and 502.

A comparison of the characteristic decay of the mixture with those of pure uranium and plutonium establishes, in accordance with the invention, the following proportions:

uranium content a=92%, plutonium content b=8%.

It can be noted that, after approximately 50 seconds, the experimental points are close to the background noise level. Thus, for calculating the uranium and plutonium contents only the first 15 intervals are retained.

It is thus clear that, by virtue of the method of the invention, the proportions of uranium and plutonium in a radioactive waste package can be known with a precision of around ±10%.

Better information still can be obtained by taking particular steps for reducing the background noise of the measurement.

For example, the object to be examined and the package can be placed in an enclosure whose walls have at least two layers of moderator separated by a layer of cadmium. This further reduces the influence of neutrons generated outside the package.

What is claimed is:

1. A method of measuring relative proportions of uranium and plutonium in a body (16, 116), including the following steps:

a) irradiating the body with photons whose energy is sufficient to cause photofission of actinide elements, b) counting the number of delayed neutrons emitted per unit time by fission products induced in the said body in response to the irradiation, c) establishing a time decay function (500) of the number of neutrons $n_e(t)$ emitted, characteristic of the actinide composition of the said body, d) comparing the time decay $n_e(t)$ characteristic of the actinide composition of the said body (116), with time decays (501, 502) of emission of delayed neutrons $n_u(t)$, $n_p(t)$ characteristic respectively of uranium and plutonium, in order to establish the relative proportions of these elements in the body.

2. A method according to claim 1, in which step d) further includes the determination of the relative proportions of uranium and plutonium, coefficients a and b, respectively in said body; wherein said coefficients are determined by $n_e(t)=an_u(t)+bn_p(t)$.

3. A method according to claim 2, in which the coefficients a and b are determined by a so-called least squares calculation method.

4. A method according to claim 1, in which the body is continuously irradiated.

5. A method according to claim 1, in which the said body is irradiated by means of a train of photon pulses.

6. A method according to claim 1, in which steps a) and b) are repeated several times.

* * * * *

UNITED STATES PATENT AND TRADEMARK OFFICE
CERTIFICATE OF CORRECTION

PATENT NO.    : 6,452,992 B1
DATED         : September 17, 2002
INVENTOR(S)   : Krzysztof Umiastowski It is certified that error appears in the above-identified patent and that said Letters Patent is hereby corrected as shown below:

<u>Title page,</u>
Item [30], please delete "Jun. 7, 1997", and insert therefor -- Jun. 6, 1997 --.

Signed and Sealed this

Tenth Day of December, 2002

JAMES E. ROGAN
*Director of the United States Patent and Trademark Office*